United States Patent [19]

Jayaram

[11] Patent Number: 5,902,792
[45] Date of Patent: May 11, 1999

[54] METHOD OF INDUCING APOPTOSIS IN CANCER CELLS

[75] Inventor: Hiremagalur N. Jayaram, Indianapolis, Ind.

[73] Assignee: Advanced Research & Technology Institute, Bloomington, Ind.

[21] Appl. No.: 08/862,015

[22] Filed: May 22, 1997

[51] Int. Cl.$^6$ ..................................... A01N 43/04

[52] U.S. Cl. ............................... 514/23; 436/64

[58] Field of Search ................................. 514/23; 436/64

[56] References Cited

PUBLICATIONS

Gharehbaghi et al, Int. J. CAncer vol. 56 p. 892, 1994.
Gharehbaghi et al, Biochemical Pharmacology vol. 48 p. 1413, 1994.
Johnson et al, Cancer Treatment Reviews vol. 2 p. 1, 1975.

*Primary Examiner*—Sheela Huff
*Attorney, Agent, or Firm*—Watov & Kipnes, P.C.

[57] ABSTRACT

A method of inducing apoptosis in apoptosis-inducible cancer cells by administering thereto an apoptosis-inducing effective amount of the compound benzamide riboside or salts thereof.

20 Claims, 3 Drawing Sheets

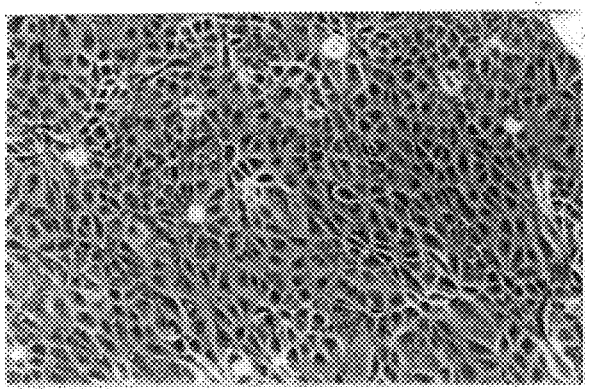
FIG. IA
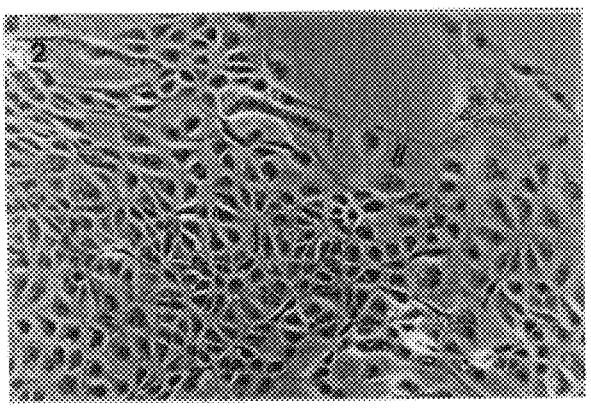
FIG. IB
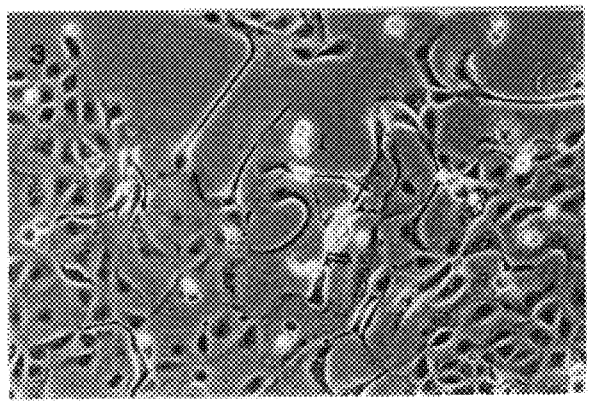
FIG. IC
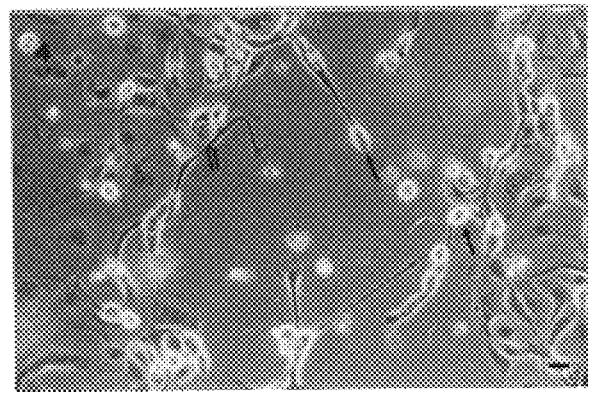
FIG. ID

METHOD OF INDUCING APOPTOSIS IN CANCER CELLS

FIELD OF THE INVENTION

The present invention is directed to a method of inducing apoptosis or programmed cell death in tumor cells by the administration of an effective amount of benzamide riboside or salts thereof.

BACKGROUND OF THE INVENTION

Compounds shown to be effective in the treatment of cancer cells typically affect such cells by inducing maturation (i.e. slowing growth) of the cells or by killing the cells (i.e. necrosis), because the compound itself is toxic. Compounds which slow cancer cell growth or are toxic to the cancer cells are often disadvantageous because the compounds themselves often adversely affect normal cells.

It has been discovered that cancer cells can be induced to kill themselves (i.e. to undergo programmed cell death, hereinafter referred to as "apoptosis"). Accordingly, compounds which can induce cancer cells to kill themselves are less likely to adversely affect the patient because the compound affects normal cells to significantly less of a degree than cancer cells (i.e. normal cells are able to recover at doses which are effective for the treatment of cancer cells).

More specifically, the process of necrosis is characterized by the inflammation of a colony of cells which include both cancer and normal cells. When cells are contacted with a necrosis-inducing agent, the cells breakdown into relatively large fragments with DNA typically withstanding any significant fragmentation (i.e. DNA being typically greater than 100,000 bases). Thus, both cancer cells and normal cells are affected.

The mechanism of apoptosis is not clearly understood. It is believed that apoptosis arises due to a change in the gene expression in the cell causing the cell to program and induce its own death. The result is a breakup of the genetic messenger, DNA, into smaller enveloped components which can be absorbed by adjacent cells without harmful effect.

Apoptosis is characterized by the selective programmed destruction of cancer cells into relatively small fragments with DNA becoming highly fragmented (i.e. the resulting fragments typically have no more than about 200 bases.) During apoptosis, cell shrinkage and internucleasomal DNA cleavage occurs, followed by the fragmentation of the DNA. Eventually the cell disintegrates into small fragments.

Thus, there is a significant difference in the results achieved by necrosis as compared with apoptosis. The cellular material remaining after necrosis is large and relatively difficult for unaffected cells to assimilate. In the aftermath of apoptosis, because the remaining material is in relatively small units, they are readily assimilated by unaffected cells.

Thus apoptosis-inducing agents possess significant advantages over compounds which induce necrosis. Such agents are not only selective for cancer cell destruction, but also enable the fragmented cellular material to be safely assimilated by the body.

Benzamide riboside has been shown to be a compound capable of inducing differentiation of cancer cells. More specifically, benzamide riboside has been shown to be cytotoxic to S49.1 lymphoma cells by Karsten Krohn et al., *J. Med. Chem.*, Vol. 35, pp 511–517 (1992) and to human myelogenous leukemia cells by Hiremagalur N. Jayaram et al., *Biochem. Biophys. Res. Commun.*, Vol. 186, No. 3, pp. 1600–1606 (1992), each of which is incorporated herein by reference.

As indicated in H. N. Jayaram et al., benzamide riboside inhibits the enzyme inosine 5'-monophosphate dehydrogenase (IMP dehydrogenase) which is necessary for cell growth. However, in vitro inhibition of IMP dehydrogenase requires very high concentrations of benzamide riboside, suggesting that the compound may require conversion to a different form to exert IMP dehydrogenase inhibitory activity. Accordingly, benzamide riboside has been described as a prodrug.

More recently, Kamran Gharehbaghi et al. *Int. J. Cancer*, Vol. 56, pp. 892–899 (1994) disclosed that benzamide riboside exhibited significant cytotoxicity against a variety of human tumor cells in culture through a derivative of benzamide riboside, benzamide adenine dinucleotide (BAD).

The references discussed above show that benzamide riboside acts through its dinucleotide derivative. While an inhibition of cell growth was observed, there was no reported observation of apoptosis. This is because human myelogenous leukemia K562 cells used for these studies possess a genetic makeup which is strongly resistant to apoptosis. Therefore, the work done to date on benzamide riboside has focused on inhibition of cell growth through reduction of IMP dehydrogenase and not to a method of inducing cells to undergo apoptosis, which is clearly an advantageous process for cancer cell destruction.

SUMMARY OF THE INVENTION

The present invention is directed to a method of inducing apoptosis in apoptosis-inducible cancer cells. The method comprises administering to said apoptosis-inducible cancer cells an apoptosis-inducing effective amount of benzamide riboside or salts thereof.

The administration of benzamide riboside in effective amounts to targeted cancer cells results in a breakdown of the targeted cancer cells without a corresponding breakdown of normal cells. This is because the normal cells are able to recover from the administration of benzamide riboside at levels sufficient to breakdown the cancer cells.

BRIEF DESCRIPTION OF THE DRAWINGS

The following drawings are illustrative of embodiments of the invention and are not intended to limit the invention as encompassed by the claims forming part of the application.

FIG. 1A is a photograph of control cells grown in the presence of saline;

FIGS. 1B–1D are photographs showing the progression of apoptosis induced by the administration of benzamide riboside from onset to an advanced stage in human ovarian carcinoma N.1 cells;

DETAILED DESCRIPTION OF THE INVENTION

Figure 2A:
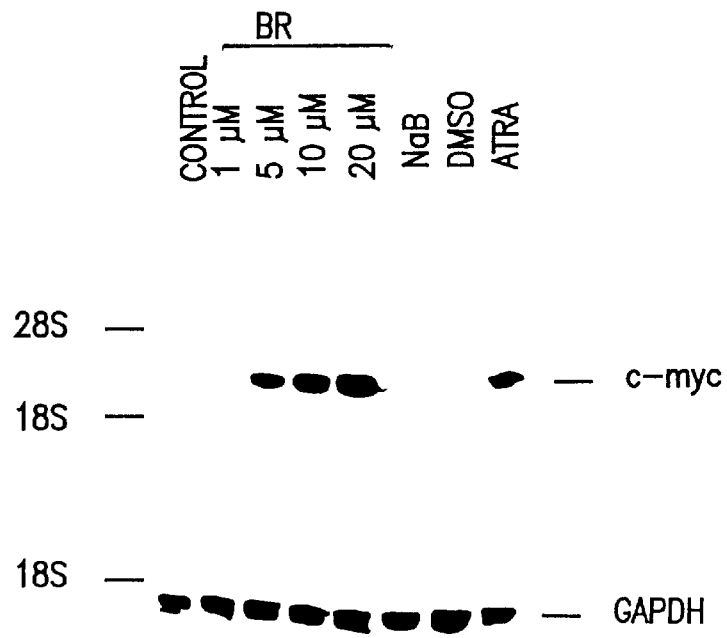
FIG. 2A is a schematic representation of the dose-dependent up-regulation of c-myc transcript levels in human ovarian carcinoma N.1 cells treated with benzamide riboside after 24 hours.

Benzamide riboside has been described as an inhibitor of cell growth and/or differentiation by inhibiting IMP dehydrogenase which catalyzes the formation of xanthine 5'-monophosphate (XMP) from inosine 5'-monophosphate (IMP). The inhibition of IMP dehydrogenase adversely affects the synthesis of guanine nucleotides and thus limits the cells ability to grow and/or differentiate.

In accordance with the present invention, benzamide riboside when delivered in a specified concentration range, can affect the DNA of apoptosis-inducible cancer cells to cause a change in the genetic makeup which programs the cell to undergo apoptosis. In particular, the administration of benzamide riboside appears to result in a sustained expression of c-myc proto-oncogene and a down regulation of the cell cycle gene cdc25A which is believed to interrupt the cell cycle progression causing conditions suitable for apoptosis.

The administration of benzamide riboside to select cancer cells (i.e. cancer cells which can be induced to undergo apoptosis) is characterized by DNA fragmentation as evidenced by a laddering effect on polyacrylamide gel and a concurrent down-regulation of the $G_1$ phase specific gene, cdc25A, expression in cancer cells.

The cancer cells which may be treated in accordance with the present invention are those that are capable of being induced to undergo chronic apoptosis (i.e. capable of being programmed themselves). Some cancer cells (i.e. human myelogenous leukemia K562 cells) possess the gene bcr-abl which prevents apoptosis even in the presence of an apoptosis-inducing agent. Unless the anti-apoptosis gene can be regulated, such cancer cells (i.e. human myelogenous leukemia K562 cells) can not be induced to undergo apoptosis by the administration of benzamide riboside. It has also been observed that cells in which the gene bcl 2 expression levels are increased and/or the gene p53 is expressed are also resistant to the induction of apoptosis.

There are, however, many types of cancer cells that are susceptible to apoptosis through the administration of benzamide riboside and are therefore within the scope of the present invention. Such cells include ovarian carcinoma, breast carcinoma, CNS carcinoma, renal carcinoma, lung cancer cells, leukemia cells, such as human promyelocytic leukemia cells, and the like.

The amount of benzamide riboside administered to the apoptosis-inducible cancer cells will be at least 5 micromoles based on a cancer cell population of approximately one million cells (hereinafter referred to as "per one million cancer cells"). A preferred concentration range for benzamide riboside is from about 5 micromoles to 25 micromoles per one million cancer cells. Most preferred is a concentration range of from about 10 micromoles to 20 micromoles, per one million cancer cells.

Benzamide riboside can be administered to a warm blooded animal in the form of pharmaceutically acceptable salts. Included among these salts are sodium sulfate, ammonium sulfate, ammonium chloride, calcium chloride, calcium sulfate and the like.

Benzamide riboside can be administered in combination with pharmaceutically acceptable carriers in the form of a pharmaceutically acceptable composition. Such carriers include mannose, glucose and balanced salt solutions. The compositions containing benzamide riboside including carriers can be lyophilized by adding sterile water as described in Lawrence A. Trissel et al., "The Handbook on Injectable Drugs", 8$^{th}$ Edition, published by the American Society of Hospital Pharmacists (1994), incorporated herein by reference.

The compositions can be administered intravenously, or orally. Oral administration of the composition is preferably carried out by using conventional inert carriers such as mannitol, sodium chloride and/or the calcium carbonate salt form of benzamide riboside.

Benzamide riboside and salts thereof are administered in a therapeutically effective dose depending on the cancer to be treated. Generally, the dosage of benzamide riboside and salts thereof is in the range of from about 1 to 10 mg/kg/day which is administered in at least one dosage form per day. The daily dosage is preferably administered intravenously or orally for five to ten days. When administered intravenously, the preferred daily dosage period is from about one to two hours.

In a preferred form of the invention, benzamide riboside is encapsulated in liposomes prepared according the Francis Zoke, Jr. et al., *Eroc. Natl. Acad. Sci.* vol. 75, pp. 4194–4198 (1978), incorporated herein by reference.

A typical product of benzamide riboside encapsulated in liposomes contains 33 µmol of cholesterol in 1.0 ml of aqueous phase (phosphate buffered saline) and 3 ml of solvent (e.g. diethyl ether, isopropyl ether, halothane or trifluorotrichloroethane). These ratios are maintained for maximum capture. When vesicles are formed from Palsub2 PpdCho, and additional 3 ml of chloroform or 0.8 ml of methanol is added to the preparation, and the vesicles are allowed to remain at 45° C. for at least 30 minutes after evaporation of the solvent. To determine the amount of encapsulated benzamide riboside or salt thereof, the vesicles are dialyzed overnight against 300 volumes of phosphate buffered saline.

EXAMPLE 1

Cell Culture

The monoclonal human ovarian adenocarcinoma cell line N.1 which is a derivative of the heterogenous cell line HOC-7 [malignant ascites of a patient with serious well-differentiated stage III adenocarcinoma of the ovary, R. N. BUICK et al., "Comparative Apoptosis of Five Adeno-Carcinoma Cell Lines," *Canc. Res.*, Vol. 45 pp 3668–3676 (Aug. 1985)] was cultured in minimum essential medium (MEM) supplemented with 10% fetal calf serum (GIBCO, Paisley, UK) at 37° C. in a humidified atmosphere containing 5% $CO_2$.

Northern Blot Analysis

The N.1 cells were grown in T-25 flasks to 90% confluency before continuous exposure to benzamide riboside and experiments were terminated by removing the drug containing medium, washing twice with ice cold phosphate-buffered saline (PBS), and subsequently lysing with RNAzol (Bio Tex, Houston, Tex.). Total RNA (30 µg/slot) was separated on a 1% agarose gel containing formaldehyde and transferred to Millipore S membranes (Millipore, Bedford, Mass.) by the capillary method. Biotinylated probes were allowed to hybridize to filter-bound RNA at 67° C. overnight. Biotinylation procedures and filter processing were done as described in G. Krupitza et al., *Brit. J. Cancer*, Vol.

72, pp. 35–40 (1995). Filters were then exposed to Kodak X-ray films (Rochester, N.Y.).

DNA Analysis

Cells were cultured in T-25 flasks and detached cells were centrifuged and lysed in 400 μl of a buffer containing 50 mM Tris-HCl pH 8.0, 10 mM EDTA, 0.5% sodium lauryl sarcosine. The majority of the adherent cells (100% in untreated controls-control cells are those grown in the presence of saline) were lysed in the same buffer (1200 μl). An aliquot of 400 μl of both types of lysates (from adherent and detached cells) were treated with 2 μl RNAse A (11 U/μl, USB, Cleveland, Ohio) for 1 hour at 37° C., followed by the addition of 10 μl of proteinase K (15 mg/ml; Bohringer Mannheim, Germany) and further incubation for 3 hours at 50° C. Equal amounts of phenol:chloroform:isoamyl alcohol (25:24:1) were added and the DNA was gently extracted in a conventional manner (wide-bore pipets, no vortexing). After two washings with chloroform: isoamyl alcohol (24:1), DNA was precipitated with alcohol, and resuspended in 30 μl of a mixture of 10 mM Tris-HCI and 1 mM EDTA having a pH of 7.5 and 2 μl RNAse (2 U/μl). The lysates derived from adherent and detached cells were pooled, the DNA content quantified and equal amounts of pooled DNA subjected to separation on 2% agarose gels.

Administration of Benzamide Riboside

The thus developed human ovarian carcinoma N.1 cells were divided into four samples (i.e. a Control Sample and Samples 1, 2, and 3) with each sample containing approximately one million cells. The Control Sample containing cancer cells grown in the presence of saline was indicative of 100% confluency (See FIG. 1A). Samples 1–3 were incubated with 5,10 and 20 micromoles benzamide riboside respectively, as soon as they reached approximately 25% confluency after seeding (FIGS. 1B–1D). A separate sample (not shown) was incubated with one micromole of benzamide riboside. After seventy-two hours of treatment no effect was observed. Dose dependent morphological changes were induced following exposure to 5 micromole (See FIG. 1B), 10 micromole (See FIG. 1C) and 20 micromole (See FIG. 1D) concentrations of benzamide riboside, respectively.

Referring to FIGS. 1B–1D, the benzamide riboside mediated phenotypic changes could be typically split into three different phases. In the first phase there was enlargement of cells with duplication or triplication of nuclei (indicated by a double arrow:⇒). An increase in cell size was also observed when N.1 cells were treated with dimethyl sulfoxide (DMSO), sodium butyrate (NaB) or with a reduction of fetal calf serum in the medium to 1.5%, which might partly reflect a status of differentiation and growth retardation. Moreover, nuclear multiplication was triggered only by NaB. In fact, only NaB causes effective cell growth arrest, whereas total serum withdrawal or incubation with 5 micromoles of benzamide riboside still permitted slow N.1 proliferation (see FIG. 1B, which shows cells at 80–90% confluency).

In an early phase, the addition of 5 micromoles benzamide riboside to N.1 cell cultures induced morphologic differentiation as shown in FIG. 1B. The occurrence of double- and triple-nucleated cells after treatment with 5, 10 or 20 micromoles of benzamide riboside could have been caused by an arrest in cell cycle progression at late M-phase(mitotic-phase), because DNA was synthesized leading to the formation of nuclei, but cytokinesis was abrogated. This phenotype was only observed in a small population of cells which might be indicative of incomplete growth retarding activity exerted by benzamide riboside. Accurate determination of proliferation was biased because the benzamide riboside-mediated effect on growth inhibition was overlapped by subsequent benzamide riboside-mediated apoptosis. Thus, growth inhibition, which might be due to limited availability of GTP and dGTP to cells following benzamide riboside treatment, could only be followed by microscopic examination. Exposure of N.1 cells to increasing concentrations of benzamide riboside for 48 to 72 hours (See for example, FIGS. 1C and 1D) revealed a second stage which has not been previously observed with N.1 cells incubated with other morphogens and differentiation inducers, such as DMSO, NaB, or low serum.

Cell death with the morphology of apoptosis was observed when N.1 cells were exposed to 10 and 20 micromoles of benzamide riboside for 72 hours as shown in FIGS. 1C and 1D, respectively. Similar morphologic changes were noticeable when N.1 cells were exposed to 5 micromoles benzamide riboside for 120 hours. As shown by way of example in FIG. 1D, single arrows (→) identify cells undergoing apoptosis. This was striking, since apoptosis was induced in N.1 cells despite the presence of 10% fetal calf serum which is known to promote cell growth.

When the N.1 cells were exposed to 10 or 20 micromoles of benzamide riboside for 6 to 7 days, necrosis of the cells was observed, indicated by dislodging of the remaining cells from the walls of the tissue culture flask, as sheets of cells.

Figure 2B:
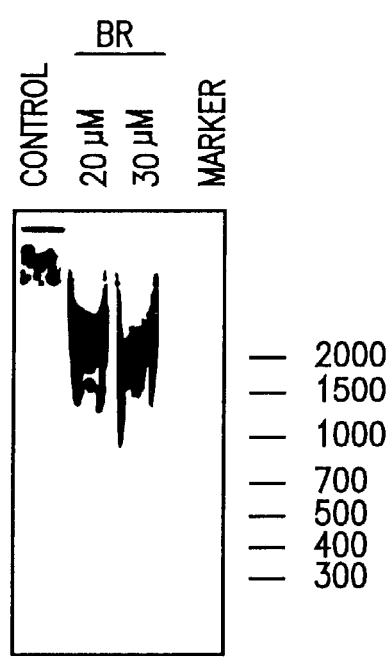
FIG. 2B is a representation of the change in DNA structure caused by the administration of benzamide riboside to human ovarian carcinoma N.1 cells after 72 hours.

It has been observed that apoptosis always correlates with the induction of c-myc proto-oncogene. In contrast, blocking c-myc expression, for example with NaB or genistein, also prevents apoptosis even when a strong apoptotic stimulus, such as 10 micromoles of all-trans retinoic acid or 40 ng/ml TNF-a was applied. Accordingly, c-myc mRNA expression was analyzed following 24 hour incubation of N.1 cells with 5, 10 and 20 micromoles of benzamide riboside. There was a dose-dependent up-regulation of c-myc transcript levels as shown in FIG. 2A. In addition, fragmentation of the DNA which is typical of apoptotic DNA degradation resulted after 72 hours of benzamide riboside treatment as shown in FIG. 2B. Therefore, induction of apoptosis by benzamide riboside was evident even in the presence of 10% fetal calf serum.

Figure 3A:
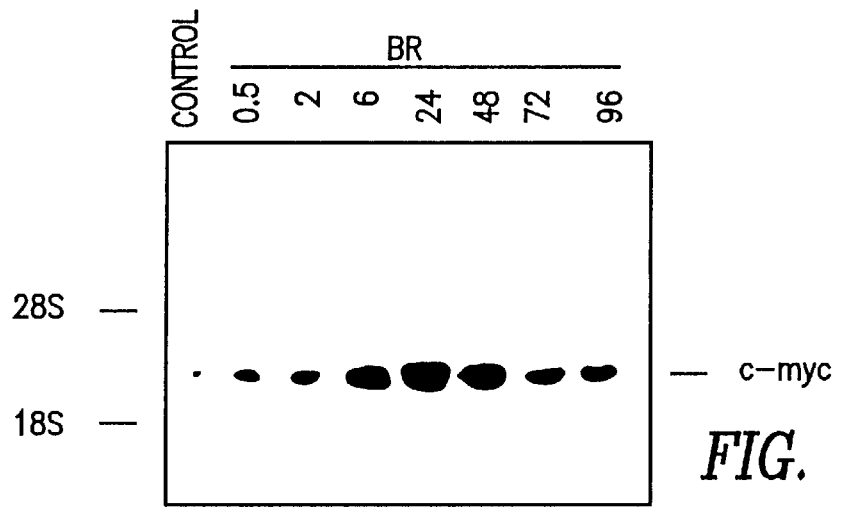
FIG. 3A shows the change in c-myc levels over time in human ovarian carcinoma N.1 cells treated with benzamide riboside.
Figure 3B:
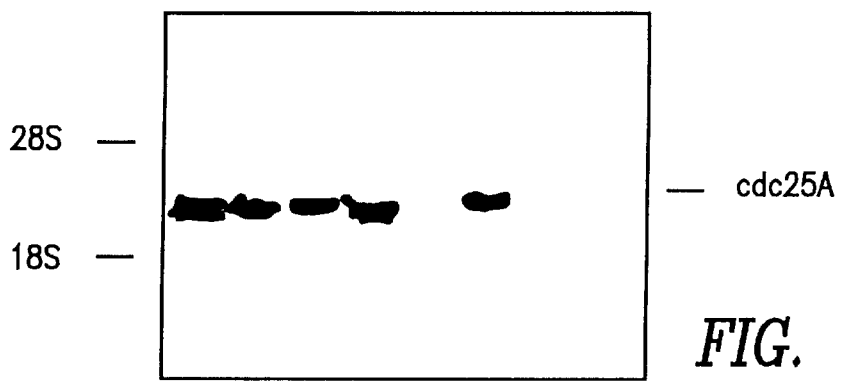
FIG. 3B shows the changes in expression levels of the gene cdc25A in human ovarian carcinoma N.1 cells treated with benzamide riboside over time.
Figure 3C:
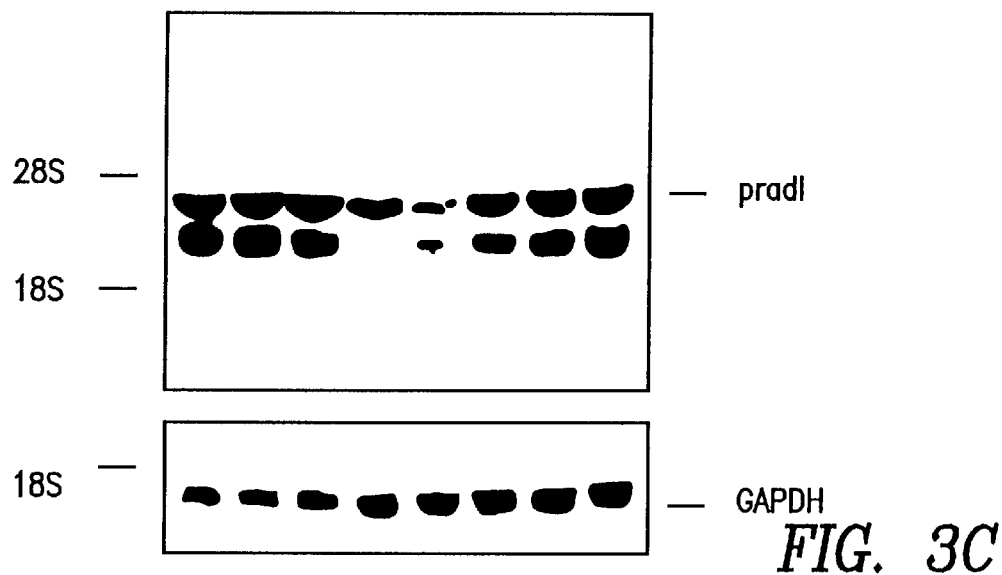
FIG. 3C shows that benzamide riboside treatment selectively down regulates cdc25A gene expression which is believed to interrupt cell cycle progression, and is not a generalized effect. Another gene involved in cell cycle progression, prad 1, is not affected by benzamide riboside treatment. The constant expression of GAPDH (glyceraldehyde 3-phosphate dehydrogenase) levels under various treatment conditions is presented to authenticate the technique.

Although c-myc up-regulation, DNA fragmentation, and morphology of dying cells were sufficient to categorize benzamide riboside as an inducer of apoptosis in N.1 cells, the phenotype before actual programmed cell death suggested that the drug was acting as an inducer of differentiation. To understand the reasons for N.1 cell growth inhibition exerted by benzamide riboside, the expression of two relevant cell cycle genes, cyclin D1/prad1 and cdc25A, which are required for the successful passage through the $G_1$ phase and are sometimes overexpressed in cancer cells, were examined and correlated with c-myc expression kinetics and the results are shown in FIGS. 3A–3C. Although, c-myc induction reached its maximum after 24 hours exposure of N.1 cells to 25 micromoles of benzamide riboside in medium containing 10% fetal calf serum (see FIG. 3A), there was only a minor and transient down-regulation of cyclin D1/prad1 mRNA expression (see FIG. 3C), which returned to normal levels after 48 hours. This result suggests that prolonged IMPDH inhibition exerted by benzamide riboside may not influence mRNA synthesis. However, cdc25A transcript levels were gradually down regulated with a transient recovery at 48 hours as shown in FIG. 3B. Therefore, the increased expression of c-myc by benzamide riboside in N.1 cells appears to promote cell cycle progression from $G_0$ to $G_1$ phase, whereas down-regulation of cdc25A interrupts cell cycle progression from $G_1$ to S phase which appears to create a pre-apoptotic condition.

What is claimed:

1. A method of inducing apoptosis in apoptosis-inducible cancer cells comprising administering to said apoptosis-inducible cancer cells an apoptosis-inducing effective amount of a compound selected from the group consisting of benzamide riboside and salts thereof.

2. The method of claim 1 wherein the apoptosis effective amount of said compound is at least 5 micromoles based on a cancer cell population of approximately one million cancer cells.

3. The method of claim 1 wherein the apoptosis effective amount of said compound is from about 5 micromoles to 25 micromoles per approximately one million cancer cells.

4. The method of claim 1 wherein the apoptosis effective amount of said compound is from about 10 micromoles to 20 micromoles per approximately one million cancer cells.

5. The method of claim 1 wherein the compound is benzamide riboside.

6. The method of claim 1 wherein said cancer cells are present in a warm blooded animal.

7. The method of claim 6 wherein said compound is administered intravenously or orally.

8. The method of claim 7 wherein said compound is administered in an amount of from about 1 to 10 mg/kg/day.

9. The method of claim 8 wherein said compound is administered at least once per day for five to 10 days.

10. The method claim 9 wherein said compound is administered intravenously over a period of from one to two hours.

11. The method of claim 1 where said compound is in the form of a pharmaceutical composition including a pharmaceutically acceptable carrier.

12. A method of inducing apoptosis in apoptosis-inducible cancer cells in vitro comprising administering to said apoptosis-inducible cancer cells an apoptosis-inducing effective amount of a compound selected from the group consisting of benzamide riboside and salts thereof.

13. The method of claim 12 wherein the apoptosis effective amount of said compound is at least 5 micromoles based on a cancer cell population of approximately one million cancer cells.

14. The method of claim 12 wherein the apoptosis effective amount of said compound is from about 5 micromoles to 25 micromoles per approximately one million cancer cells.

15. The method of claim 12 wherein the apoptosis effective amount of said compound is from about 10 micromoles to 20 micromoles per approximately one million cancer cells.

16. The method of claim 12 wherein the compound is benzamide riboside.

17. The method of claim 12 wherein said cancer cells are ovarian cancer cells.

18. The method of claim 17 wherein the ovarian cancer cells are human ovarian carcinoma N.1 cells.

19. The method of claim 1 comprising inducing apoptosis by inhibiting the normal function of the cdc25A gene.

20. The method of claim 12 comprising inducing apoptosis by inhibiting the normal function of the cdc25A gene.

* * * * *